(12) United States Patent
Fang et al.

(10) Patent No.: US 12,678,132 B2
(45) Date of Patent: Jul. 14, 2026

(54) LOCKING DEVICE FOR SCANNING ASSEMBLY OF ULTRASOUND IMAGING APPARATUS AND ULTRASOUND IMAGING APPARATUS

(71) Applicant: GE Precision Healthcare LLC, Waukesha, WI (US)

(72) Inventors: Donghui Fang, Wuxi (CN); Qiang Yao, Wuxi (CN); Bo Dan, Wuxi (CN); Junjian Meng, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/175,563

(22) Filed: Apr. 10, 2025

(65) Prior Publication Data

US 2025/0318804 A1 Oct. 16, 2025

(30) Foreign Application Priority Data

Apr. 10, 2024 (CN) .......................... 202410430618.5

(51) Int. Cl.
*A61B 8/00* (2006.01)
*A61B 8/08* (2006.01)

(52) U.S. Cl.
CPC .......... *A61B 8/4218* (2013.01); *A61B 8/0825* (2013.01); *A61B 8/403* (2013.01); *A61B 8/4405* (2013.01); *A61B 8/4455* (2013.01)

(58) Field of Classification Search
CPC ....... A61B 8/42; A61B 8/4209; A61B 8/4218; A61B 8/4405; A61B 8/4411; A61B 90/50; A61B 17/2255; A61B 5/6835; A61B 1/00149; F16M 11/14
See application file for complete search history.

(56) References Cited

U.S. PATENT DOCUMENTS

| | | | | |
|---|---|---|---|---|
| 6,102,679 A | * | 8/2000 | Brown | .................... F04B 41/02 91/422 |
| 6,491,273 B2 | * | 12/2002 | King | ...................... A61B 90/50 403/90 |

FOREIGN PATENT DOCUMENTS

| | | |
|---|---|---|
| CN | 214231370 U | 9/2021 |
| CN | 215778210 U | 2/2022 |

* cited by examiner

*Primary Examiner* — Carolyn A Pehlke

(57) ABSTRACT

An ultrasound imaging apparatus and a locking apparatus for a scanning assembly in the ultrasound imaging apparatus. The locking apparatus includes: a scanning assembly connecting apparatus, one end of which has a ball-head structure and the other end of which is connected to the scanning assembly; a fixing member, connected to a main body of the ultrasound imaging apparatus, and including a hollow cavity, the ball-head structure being accommodated within the hollow cavity and movable within the hollow cavity; and a pressing assembly, including a motor assembly, a cylinder assembly, and a pressing member, the cylinder assembly being disposed between the motor assembly and the pressing member, and cylinder gas pressure of the cylinder assembly being increased under the driving of the motor assembly, to drive the pressing member to press against the ball-head structure, thereby locking the scanning assembly.

15 Claims, 5 Drawing Sheets

LOCKING DEVICE FOR SCANNING ASSEMBLY OF ULTRASOUND IMAGING APPARATUS AND ULTRASOUND IMAGING APPARATUS

CROSS-REFERENCE TO RELATED APPLICATION

This application claims priority to Chinese Patent Application No. 202410430618.5, which was file on Apr. 10, 2024 at the Chinese Patent Office. The entire contents of the above-listed application are incorporated by reference herein in their entirety.

TECHNICAL FIELD

The embodiments of the present application relate to the technical field of medical instruments, and in particular, relate to a locking apparatus for a scanning assembly in an ultrasound imaging apparatus and the ultrasound imaging apparatus.

BACKGROUND

An ultrasound imaging system usually uses a scanning assembly including an ultrasound transducer to emit an ultrasound signal and receive an echo signal for imaging. The ultrasound imaging system can be used for scanning a variety of human organs and tissues.

An automated breast ultrasound scanning apparatus (ABUS) is one type of ultrasound imaging system that automatically scans a tissue to be scanned (e.g., a breast) by means of the scanning assembly. The scanning assembly is allowed to have a certain degree of freedom before scanning, so that the scanning assembly can be adjusted to a proper position. During scanning, the scanning assembly is in closely attached to the tissue to be scanned, and an operator generally needs to lock the scanning assembly for scanning, to ensure imaging quality and scanning safety. After the scanning is completed, the operator releases the locking of the scanning assembly.

At present, the locking of the scanning assembly is generally performed in a motor-driven manner. In addition, to increase stability of the locking, a motor needs to cooperate with a plurality of additional force conducting mechanisms to amplify a locking force. However, due to a limited space size, a degree of amplification of the locking force of the locking apparatus is limited. This results in a complex structure and limited reliability of the locking apparatus for the scanning assembly.

It should be noted that the above introduction of the background is only for the convenience of clearly and completely describing the technical solutions of the present application, and for the convenience of understanding for those skilled in the art.

SUMMARY

To resolve at least one of the above technical problems, embodiments of the present application provide a locking apparatus for a scanning assembly in an ultrasound imaging apparatus and the ultrasound imaging apparatus.

According to an embodiment of a first aspect of the present application, a locking apparatus for a scanning assembly in an ultrasound imaging apparatus is provided. The locking apparatus comprises:

a scanning assembly connecting apparatus, one end of which has a ball-head structure and the other end of which is connected to the scanning assembly;

a fixing member, connected to a main body of the ultrasound imaging apparatus, and comprising a hollow cavity, the ball-head structure being accommodated within the hollow cavity and movable within the hollow cavity; and a pressing assembly, comprising a motor assembly, a cylinder assembly, and a pressing member, the cylinder assembly being disposed between the motor assembly and the pressing member, and cylinder gas pressure of the cylinder assembly being increased under the driving of the motor assembly, to drive the pressing member to press against the ball-head structure, thereby locking the scanning assembly.

In one or some embodiments, the cylinder assembly comprises:

a first cylinder, provided with a first piston connected to the motor assembly, the first piston moving under the driving of the motor assembly; and a second cylinder, provided with a second piston connected to the ball-head structure;

the first cylinder being connected to the second cylinder by means of a gas passage.

In one or some embodiments, the cylinder assembly further comprises:

a first check valve, disposed in the gas passage to allow gas to flow unidirectionally from the first cylinder into the second cylinder; and a second check valve, disposed on the first piston, the second check valve being configured to be closed when the first piston compresses the gas in the first cylinder, and to be opened when the first piston retracts.

In one or some embodiments, an inner diameter of the first cylinder is smaller than an inner diameter of the second cylinder.

In one or some embodiments, the motor assembly comprises a motor, a transmission gear, and a transmission rod, the transmission gear being engaged with an output gear of the motor, and both ends of the transmission rod being connected to the transmission gear and the cylinder assembly, respectively.

In one or some embodiments, a radial dimension of the transmission gear is greater than a radial dimension of the output gear of the motor.

In one or some embodiments, the locking apparatus further comprises a pressure limiting valve disposed on the cylinder, the pressure limiting valve being opened when gas pressure in the cylinder reaches a predetermined value.

In one or some embodiments, the pressure limiting valve is a solenoid valve that can be switched between an open state and a closed state by means of a switch.

According to an embodiment of a second aspect of the present application, an ultrasound imaging apparatus is provided. The ultrasound imaging apparatus comprises the locking apparatus according to the embodiment of the first aspect.

In one or some embodiments, the ultrasound imaging apparatus further comprises:

a scanning assembly, the scanning assembly being connected to the locking apparatus and comprising a housing, an ultrasound transducer, and a control unit, the control unit being disposed outside the housing and being operable to control the locking apparatus, and the ultrasound transducer being accommodated within the housing and configured to perform ultrasound imaging.

One of the beneficial effects of the embodiments of the present application is that: under the driving of the motor assembly, the cylinder assembly drives the pressing member to press against the ball-head structure to lock the scanning assembly, so that the structure is simple and highly reliable, and costs can be reduced.

With reference to the following description and drawings, specific implementations of the embodiments of the present application are disclosed in detail, and the way in which the principles of the embodiments of the present application can be employed are illustrated. It should be understood that the embodiments of the present application are not limited in scope thereby. Within the scope of the spirit and clauses of the appended claims, the embodiments of the present application include many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and those of ordinary skill in the art may obtain other implementations according to the drawings without involving inventive effort. In the drawings.

DETAILED DESCRIPTION

Figure 1:
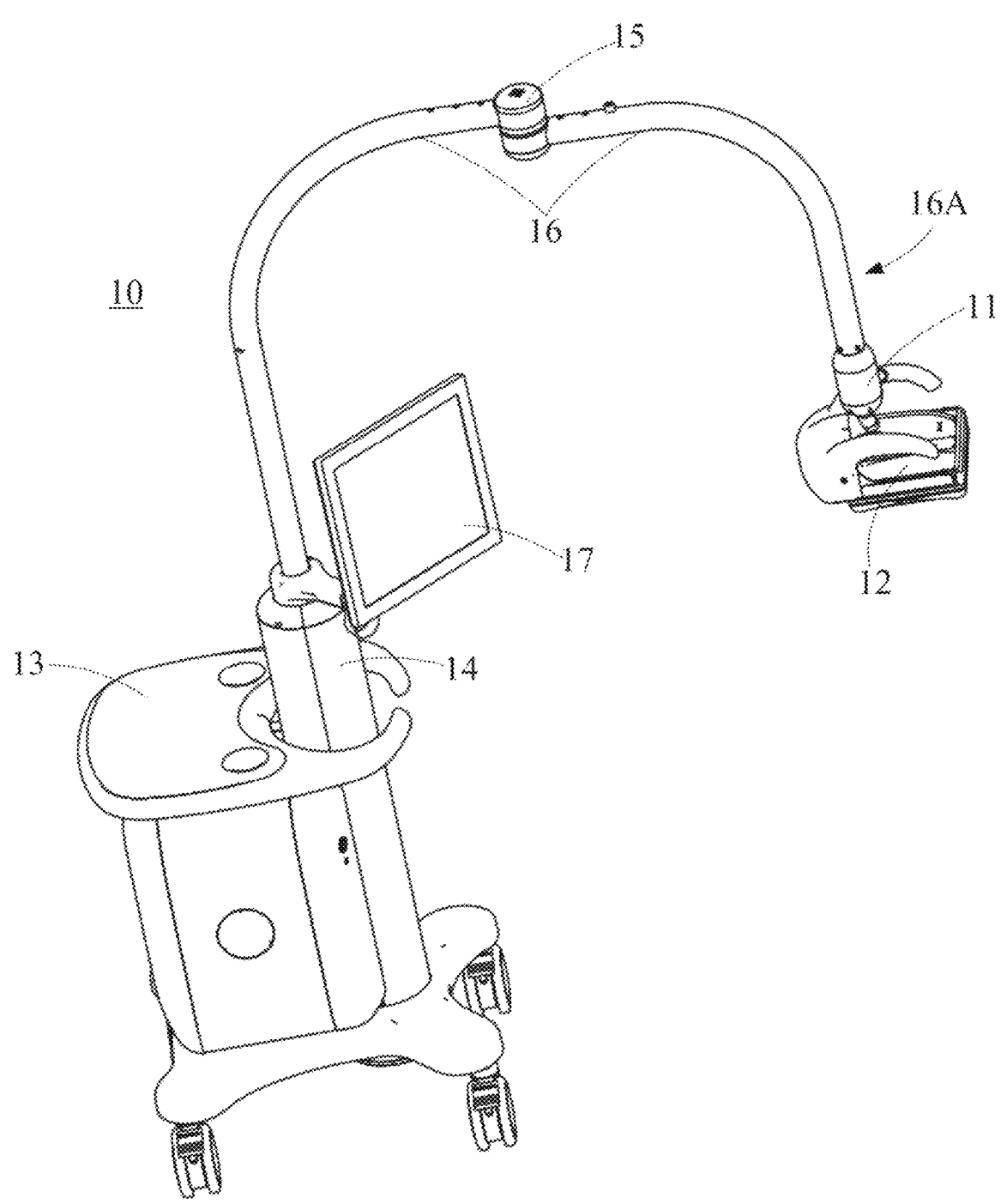
FIG. 1 is a schematic diagram of an ultrasound imaging apparatus according to an embodiment of the present application.

The foregoing and other features of the embodiments of the present application will become apparent from the following description with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms "first", "second", etc., are used to distinguish different elements, but do not represent a spatial arrangement or temporal order, etc., of these elements, and these elements should not be limited by these terms. The term "and/or" includes any and all combinations of one or more associated listed terms. The terms "comprise", "include", "have", etc., refer to the presence of described features, elements, components, or assemblies, but do not exclude the presence or addition of one or more other features, elements, components, or assemblies.

In the embodiments of the present application, the singular forms "a", "the", etc., include plural forms, and should be broadly construed as "a type of" or "a class of" rather than being limited to the meaning of "one". Furthermore, the term "the" should be construed as including both the singular and plural forms, unless otherwise specified in the context. In addition, the term "according to" should be construed as "at least in part according to . . . " and the term "based on" should be construed as "based at least in part on . . . ", unless otherwise specified in the context.

In the descriptions of the present application, it should be noted that, unless otherwise specified and defined, the terms "connected" and "connect" should be understood in a broad sense, which, for example, may be a fixed connection, a detachable connection, or an integral connection; may be a mechanical or electrical connection; and may be a direct connection or an indirect connection by means of an intermediate medium. Those of ordinary skill in the art may understand specific meanings of the foregoing terms in the present application according to a specific situation.

The features described and/or illustrated for one implementation may be used in one or more other implementations in the same or similar way, be combined with features in other embodiments, or replace features in other implementations. The term "include/comprise" when used herein refers to the presence of features, integrated components, steps, or assemblies, but does not preclude the presence or addition of one or more other features, integrated components, steps, or assemblies.

The embodiments of the present application are specifically described below.

An embodiment of the present application provides an ultrasound imaging apparatus. FIG. 1 is a schematic diagram of an ultrasound imaging apparatus according to an embodiment of the present application. FIG. 1 shows a structure of an ultrasound imaging apparatus 10 that is an ABUS as an example. However, it should be noted that although some embodiments of the present application are presented in a specified environment of human breast ultrasound, it should be understood that the present application is applicable to ultrasound scanning of any externally accessible human or animal body part (for example, abdomen, legs, feet, arms, or neck), and is also applicable to another medical imaging apparatus (for example, X-ray scanning) having a similar mechanical structure.

As shown in FIG. 1, the ultrasound imaging apparatus 10 may include an ultrasound processor housing 13 including an ultrasound processor, a frame 14, a movable and adjustable support arm (for example, an adjustable arm) 16 including a hinge joint 15, a scanning assembly 12 connected to a first end 16A of the adjustable arm 16 by means of a locking apparatus 11, and a display 17 connected to the frame 14.

In some examples, a fully functional ultrasound engine may be provided within the ultrasound processor housing 13, and is configured to drive an ultrasound transducer in the scanning assembly 12, and generate volumetric breast ultrasound data from a scan in conjunction with related position and orientation information. In some examples, volumetric scan data may be transmitted to another computer system by using any of a variety of data transmission methods known in the art for further processing, or the volumetric scan data may be processed by the ultrasound engine. A general-purpose computer/processor integrated with the ultrasound engine may further be provided for general user interface and system control. The general-purpose computer may be a self-contained stand-alone unit, or may be remotely controlled, configured, and/or monitored by remote stations connected across networks.

In some examples, a component specifically for effective weight adjustment of the scanning assembly 12 is included in the frame 14 of the ultrasound imaging apparatus 10. Specifically, one end of the adjustable arm 16 is connected to the scanning assembly 12 as shown in FIG. 1, and the other end of the adjustable arm 16 is disposed inside the frame 14. The frame 14 can be used for securing the adjustable arm 16 and guidance during up and down movement. A counterweight is further disposed inside the frame 14, and the counterweight may be connected to the other end of the adjustable arm 16 by means of a cable. The weight of the counterweight may be particularly designed, and may be approximately equal to the sum of the weights of the scanning assembly 12 and the adjustable arm 16. In such manner of configuration, the scanning assembly 12 is neutrally buoyant in space, or has a light net upward or downward weight for pressing a breast, while allowing an easy user operation. A material of the cable may be any one, for example, a steel wire, a polymer, or the like. The cable may be in the shape of a rope, or may be in the shape of a driving belt, or any other shape capable of connecting the counterweight and the adjustable arm 16. In addition, to facilitate a sliding connection between the counterweight and the adjustable arm 16, a pulley structure may be disposed in an appropriate position, to implement a smooth connection between the counterweight and the adjustable arm. As a user presses the adjustable arm 16 downward, the adjustable arm 16 moves downward. In this case, the adjustable arm 16 applies an increased upward pulling force to the counterweight by means of the cable to raise the counterweight. On the contrary, when the user lifts the adjustable arm 16 upward, the adjustable arm 16 moves upward, at which time the pressure of the adjustable arm 16 on the cable decreases and, correspondingly, the tension of the cable on the counterweight decreases, causing the counterweight to descend. As described above, the weight of the counterweight may be configured to be approximately equal to the sum of the weights of the scanning assembly 12 and the adjustable arm 16. In this way, when the user manually adjusts the positions of the adjustable arm 16 and the scanning assembly 12, due to the presence of the counterweight, it is easy to implement force balance of the scanning assembly 12 in any position, to keep a stable position.

In some examples, the adjustable arm 16 is configured and adapted so that the scanning assembly 12 is neutrally buoyant in space, or has a light net downward weight (for example, 1 kg to 2 kg) for pressing the breast, while allowing an easy user operation. In an alternative embodiment, the adjustable arm 16 may be configured so that the scanning assembly 12 is neutrally buoyant in space during positioning of a scanner on a tissue of a patient. Then, after the scanning assembly 12 is positioned, the components within the frame 14 of the ultrasound imaging apparatus 10 may be adjusted to apply a desired downward weight for breast pressing and increased image quality. For example, components such as a driving apparatus may be disposed within the frame 14 to provide an additional acting force to the counterweight within the frame 14, thereby enabling the desired downward weight to be applied to the scanning assembly. In one example, the downward weight (for example, a force) may be within a range of 2 kg to 11 kg.

In some examples, as shown in FIG. 1, the adjustable arm 16 includes the hinge joint 15. The hinge joint 15 divides the adjustable arm 16 into a first arm portion and a second arm portion. The first arm portion is connected to the scanning assembly 12, and the second arm portion is connected to the frame 14. The hinge joint 15 allows the second arm portion to rotate relative to the second arm portion and the frame 14. For example, the hinge joint 15 allows the scanning assembly 12 to translate transversely and horizontally, but not vertically, relative to the second arm portion and the frame 14. In such a manner, the scanning assembly 12 may rotate towards the frame 14 or away from the frame 14. However, this is not limited thereto. For example, the hinge joint 15 may alternatively be configured to allow the entire adjustable arm 16 (for example, the first arm portion and the second arm portion) to move vertically as a whole (for example, translating upward and downward together with the frame 14).

In some examples, the display 17 is connected to the frame 14 at an interface where the adjustable arm 16 enters the frame 14. Since the display 17 is directly connected to the frame 14 rather than the adjustable arm 16, the display 17 does not affect the weight of the adjustable arm 16 and a balancing mechanism of the adjustable arm 16. In one example, the display 17 may rotate in horizontal and transverse directions (for example, rotatable about a central axis of the frame 14), but cannot move vertically. In an alternative example, the display 17 may also be vertically movable. Although FIG. 1 illustrates the display 17 connected to the frame 14, in other examples, the display 17 may be connected to different components of the ultrasound imaging apparatus 10, such as, connected to the ultrasound processor housing 13, or positioned away from the ultrasound imaging apparatus 10.

It should be noted that, however, FIG. 1 shows only an example of a configuration and a relative position of the ultrasound imaging apparatus 10, but the configuration and the relative position are not unique. For example, a shape of the adjustable arm 16 may be a shape other than a curved shape shown in FIG. 1, such as a spiral shape, a polygonal line shape, or the like. In addition, the adjustable arm 16 may not include the hinge joint 15 but may be integrally formed or may have another type of structure.

Figure 2:
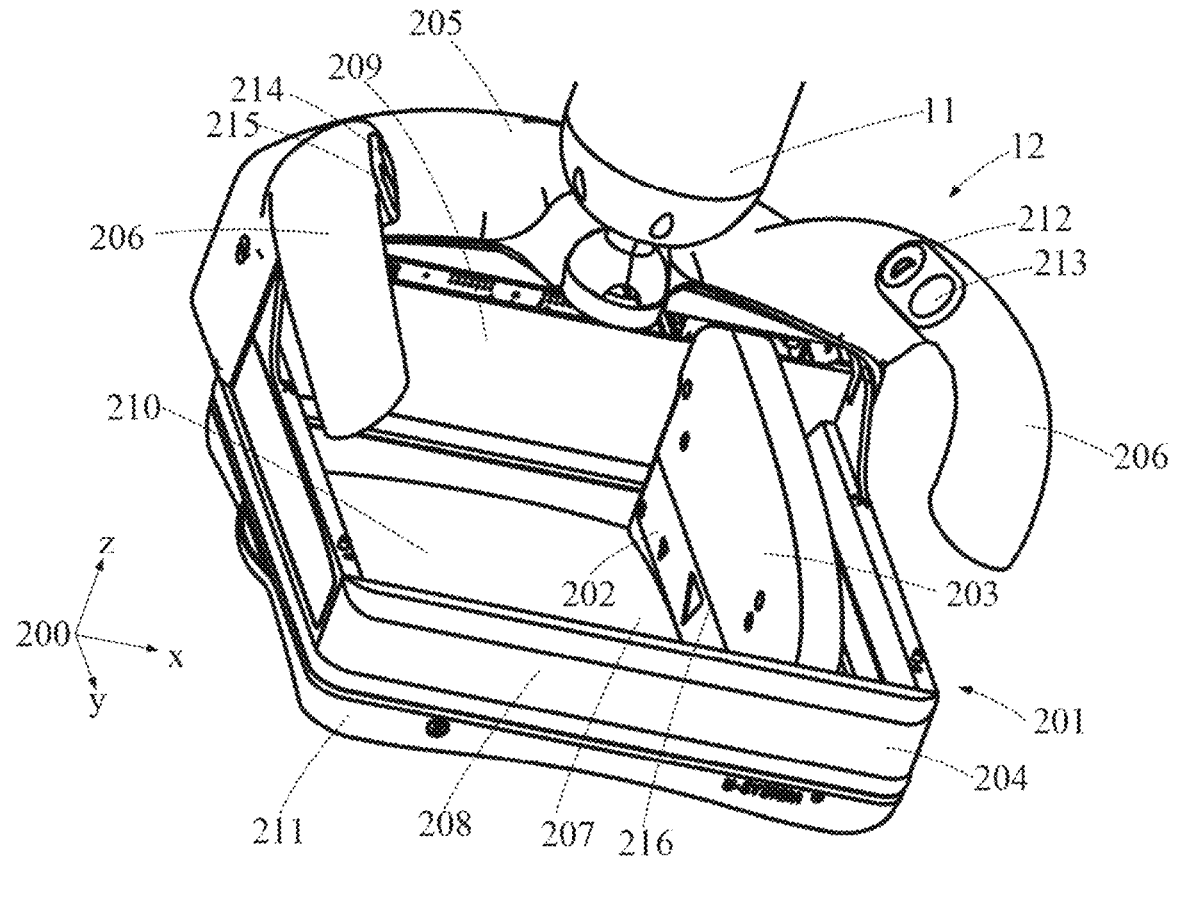
FIG. 2 is a schematic diagram of a scanning assembly connected to a locking apparatus according to an embodiment of the present application.

Next, a specific structure of the scanning assembly 12 is described by using an example. FIG. 2 is a schematic diagram of a scanning assembly connected to a locking apparatus according to an embodiment of the present application. As shown in FIG. 2, a coordinate system 200 includes a horizontal axis x, a lateral axis y, and a vertical axis z.

As shown in FIG. 2, in some examples, the scanning assembly 12 may include a housing 201, a transducer module 202, and a module receiver 203. The housing 201 may include a frame 204 and a handle portion 205, and the handle portion 205 may include two handles 206. The two handles 206 oppose each other across a transverse axis of the scanning assembly 12, and the transverse axis is centered on an adjustable arm and defined relative to the lateral axis y. The frame 204 may be rectangular, and an inner periphery of the frame 204 defines an opening 207. The opening 207 provides space (e.g., a void volume) for translating the module receiver 203 and the transducer module 202 during a scanning process. However, the present application is not limited thereto, and the frame 204 may alternatively be in another shape.

As shown in FIG. 2, in some examples, the frame 204 may include four side walls. Specifically, the frame 204 includes a front side wall 208 and a rear side wall 209, the rear side wall 209 being directly connected to the handle portion 205 of the housing 201, and the front side wall 208 being opposite to the rear side wall 209 with respect to the horizontal axis x. The frame 204 further includes a right side wall and a left side wall, the corresponding side walls opposing each other and both being in a plane defined by the vertical axis z and the lateral axis y. The frame 204 further includes a top side and a bottom side, the top side and the bottom side being defined relative to the vertical axis z, and the top side facing the adjustable arm.

Figure 3:
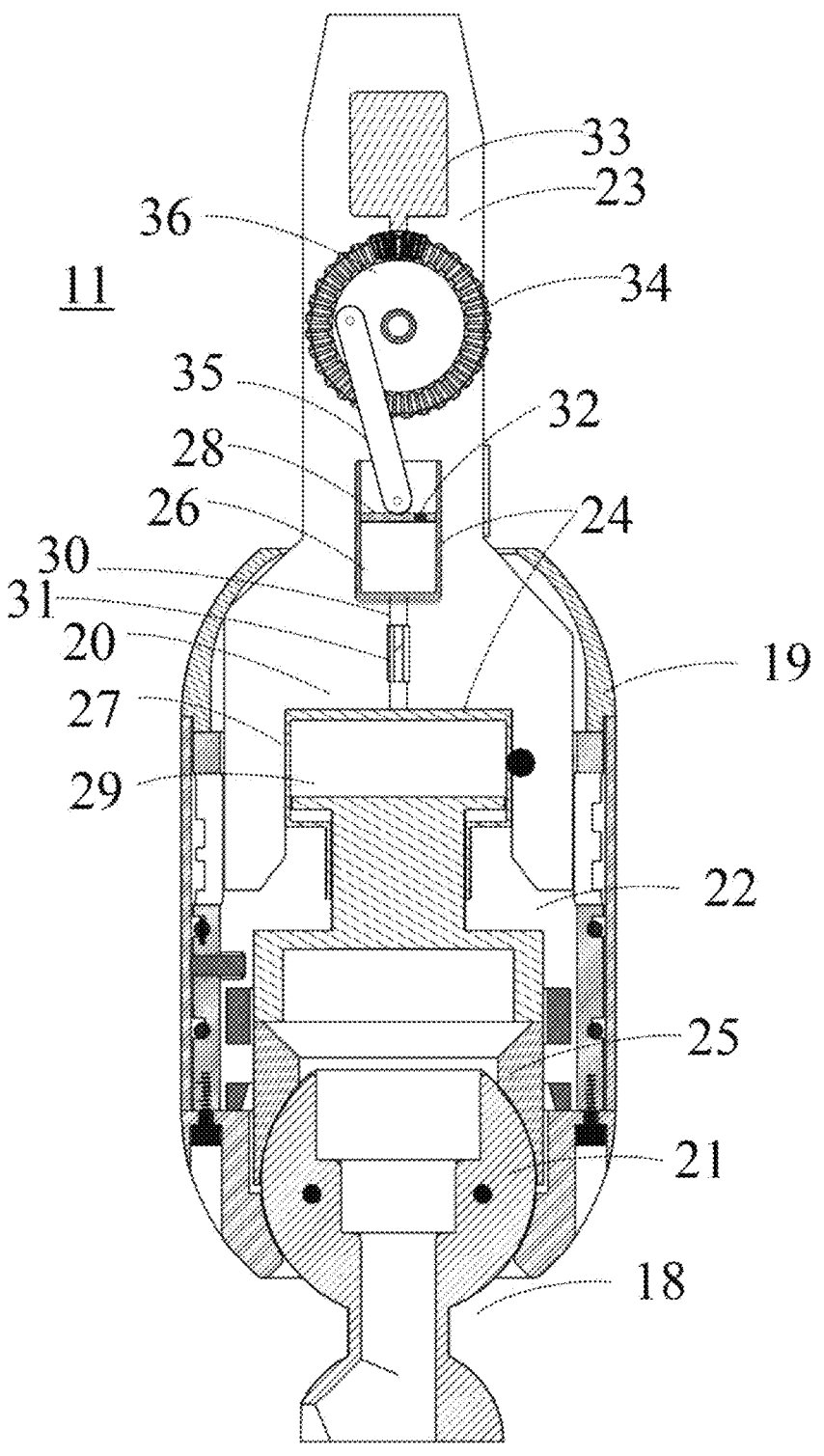
FIG. 3 is a schematic diagram of a structure of a locking apparatus according to an embodiment of the present application.

As shown in FIG. 2, in some examples, the scanning assembly 12 may further include a film 210, the film 210 being disposed across the opening 207, and the film 210 being connected to the bottom side of the frame 204. In some examples, the film 210 is a film sheet that is held tight across the opening 207. For example, the film 210 may be made from a flexible but non-stretchable material, and the material is thin, waterproof, durable, highly acoustically transparent, resistant to chemical corrosion, and/or biocompatible. A bottom surface of the film 210 may contact a tissue (e.g., a breast) during scanning, and an upper surface of the film 210 may at least partially contact the transducer module 202 during scanning. As shown in FIG. 3, the film 210 may be permanently connected to a hard-housing holding portion 211 surrounding the periphery of the film 210. The holding portion 211 is connected to the bottom side of the frame 204.

As shown in FIG. 2, in some examples, the handle portion 205 of the housing 201 includes the two handles 206 for moving the scanning assembly 12 in space and positioning the scanning assembly 12 on a tissue (e.g., on the body of a patient). In an alternative embodiment, the housing 201 may not include the handles 206. In the examples shown in FIG. 2, the handles 206 may be integrally formed with the frame 204 of the housing 201. In another example, the handles 206 and the frame 204 may be formed separately and then mechanically connected together to form the entire housing 201 of the scanning assembly 12.

As shown in FIG. 1 and FIG. 2, the scanning assembly 12 is connected to the adjustable arm 16 by means of the locking apparatus 11, and the locking apparatus 11 may include a ball joint, for example, a ball and socket connector. In some examples, as shown in FIG. 2, a top dome portion of the handle portion 205 is connected to the locking apparatus 11. In some examples, the top of the handle portion 205 may include a depression forming a socket, and a ball of the ball joint of the locking apparatus 11 may be fit in the socket. The ball joint is movable in a plurality of directions. For example, the ball joint provides rotational movement of the scanning assembly 12 relative to the adjustable arm 16, and the locking apparatus 11 may lock the ball joint to keep the scanning assembly 12 stationary relative to the adjustable arm 16. In addition, the ball joint may alternatively be configured to only rotate but not to move in a plurality of directions, such as oscillating. In addition, the ball joint may alternatively be included inside the locking apparatus 11, that is, the locking apparatus 11 and the scanning assembly are connected to each other in a mutually immovable manner. For example, the locking apparatus includes a scanning assembly connecting apparatus, one end of which has a ball-head structure or ball joint and the other end of which is connected to the scanning assembly in a mutually immovable manner. In this way, the scanning assembly 12 may rotate relative to the adjustable arm 16 when the ball-head structure or ball joint is unlocked relative to another component of the locking apparatus and the adjustable arm 16, and the scanning assembly 12 cannot move relative to the adjustable arm 16 when the ball-head structure or ball joint is locked relative to another component of the locking apparatus and the adjustable arm 16. The locking apparatus 11 is described in detail in a subsequent part.

In addition, as shown in FIG. 2, the handles 206 of the handle portion 205 may include buttons for controlling scanning and adjusting the scanning assembly 12. For example, a first handle in the handles 206 includes a first weight adjustment button 212 and a second weight adjustment button 213. The first weight adjustment button 212 may reduce a load applied to the scanning assembly 12 from the adjustable arm 16. The second weight adjustment button 213 may increase a load applied to the scanning assembly 12 from the adjustable arm 16. Increasing the load applied to the scanning assembly 12 may increase pressure and an amount of pressing applied to a tissue on which the scanning assembly 12 is placed. Furthermore, increasing the load applied to the scanning assembly increases the effective weight of the scanning assembly on the tissue to be scanned. In one example, increasing the load may press a tissue of a patient, such as a breast. In such manner, varying amounts of pressure (e.g., load) may be applied consistently with the scanning assembly 12 during scanning, to obtain a high-quality image by using the transducer module 202.

Before scanning, a user (e.g., an ultrasound technician or physician) may position the scanning assembly 12 on a patient or a tissue. Once the scanning assembly 12 is properly positioned, the user may adjust the weight (e.g., adjust an amount of pressing) of the scanning assembly 12 on the patient by using the first weight adjustment button 212 and/or the second weight adjustment button 213. Then, the user may initiate a scanning process by means of additional control on the handle portion 205 of the housing 201. For example, as shown in FIG. 2, a second handle in the handles 206 includes a first additional button 214 and a second additional button 215. The first additional button 214 is configured to initiate scanning (e.g., once the scanning assembly has been placed on a tissue/patient and an amount of pressing has been selected), the second additional button 215 is configured to stop scanning. In other words, the first additional button 214 may act as a locking button, and the user may operate the first additional button 214 after positioning of the scanning assembly 12 is completed to lock the scanning assembly 12, that is, stop lateral and horizontal movement of the scanning assembly 12 and start scanning; and the second additional button 215 may act as an unlocking button, and the user may operate the second additional button 215 after the scanning is completed to unlock the scanning assembly 12, that is, allow lateral and horizontal movement of the scanning assembly 12. It should be noted that, FIG. 2 shows that the first additional button 214 and the second additional button 215 are disposed on the handles 206 of the scanning assembly 12. However, the present application is not limited thereto. The first additional button 214 and the second additional button 215 may alternatively be disposed in other positions of the ultrasound imaging apparatus 10, for example, disposed in other positions except the handles 206 of the housing 201, or may be disposed on the locking apparatus 11. This is not limited in the present application.

In this embodiment of the present application, the housing 201 is configured to remain stationary during scanning. In other words, once the weight applied to the scanning assembly 12 is adjusted by means of the adjustable arm 16 and then the scanning assembly 12 is locked by means of the locking apparatus 11, the housing 201 may remain in a stationary position without translating in a horizontal or transverse direction. However, the housing 201 may still translate vertically as the adjustable arm 16 moves vertically. In addition, the module receiver 203 is configured to translate relative to the housing 201 during scanning. As shown in FIG. 2, the module receiver 203 may translate horizontally along the horizontal axis x relative to the housing 201. For example, the module receiver 203 may be driven to move by a motor or the like. In addition, the transducer module 202 is removably connected to the module receiver 203. Therefore, during scanning, the transducer module 202 and the module receiver 203 may translate horizontally. During scanning, the transducer module 202 may sweep horizontally across the breast under the control of the motor of the module receiver 203, and at the same time, a contact surface of the transducer module 202 contacts the film 210. The transducer module 202 and the module receiver 203 are connected together at a module interface 216. The dimensions of the module receiver 203 and the transducer module 202 in the horizontal direction may be the same or different. In some embodiments, the module interface 216 includes a connector between the transducer module 202 and the module receiver 203, the connector including mechanical and electrical connections.

It may be understood from the foregoing descriptions that, in this embodiment of the present application, the locking apparatus is very important for securing of the scanning assembly and an ultrasound imaging process. Fast and stable locking is critical for high-quality ultrasound imaging with the scanning assembly. The following example of the present application provides a locking apparatus that provides a high locking force in limited space. Next, a detailed structure of the locking apparatus is described by using an example.

An embodiment of the present application further provides a locking apparatus for a scanning assembly in an ultrasonic imaging apparatus. FIG. 3 is a schematic diagram of a structure of the locking apparatus according to this embodiment of the present application, and shows a case in which the locking apparatus is cut axially.

As shown in FIG. 3, the locking apparatus 11 includes a scanning assembly connecting apparatus 18, a fixing member 19, and a pressing assembly 20.

In this embodiment of the present application, one end of the scanning assembly connecting apparatus 18 has a ball-head structure 21 and the other end is connected to the scanning assembly. The fixing member 19 is connected to a main body of the ultrasound imaging apparatus, for example, the fixing member 19 may be connected to one end of an adjustable arm 16. The fixing member 19 includes a hollow cavity 22, and the ball-head structure 21 is accommodated within the hollow cavity 22 and is movable within the hollow cavity 22. The pressing assembly 20 includes a motor assembly 23, a cylinder assembly 24, and a pressing member 25. The cylinder assembly 24 is disposed between the motor assembly 23 and the pressing member 25, and the cylinder assembly 24 may be disposed on the main body of the ultrasound imaging apparatus, for example, disposed on the adjustable arm 16, but the present application is not limited thereto. For example, the cylinder assembly 24 may alternatively be disposed in the hollow cavity 22, or one part of the cylinder assembly 24 may be disposed on the ultrasound imaging apparatus and another part of the cylinder assembly 24 is disposed in the hollow cavity 22. This is not limited in the present application. Driven by the motor assembly 23, a cylinder gas pressure of the cylinder assembly 24 is increased, to drive the pressing member 25 to press against the ball-head structure 21, and the pressing member applies a friction force to the ball-head structure 21, thereby locking the scanning assembly.

According to the foregoing embodiment, driven by the motor assembly 23, the cylinder assembly 24 drives the pressing member 25 to press against the ball-head structure 21 to lock the scanning assembly, so that the structure is simple and highly reliable, and costs can be reduced.

For example, in contrast to a conventional structure using a motor-driven lever, a motor-driven cylinder assembly is used in this embodiment of the present application, so that pressurization can be performed continuously until a sufficient locking force is generated without using another force amplifying structure (e.g., a lever). Other potential advantages are that, since the cylinder assembly itself can implement reliable switching of a direction of a force, for example, independent of a direction of a driving force of the motor assembly, a direction of an acting force applied to the pressing member 25 by the cylinder assembly 24 is always the same. Therefore, it is not necessary to dispose an adjusting mechanism for eliminating a machining tolerance or a structure dedicated to switching a direction of an output force of a lever between the cylinder assembly and the pressing member, so that reliable locking for the scanning assembly can be implemented with a simple structure. In addition, the cylinder assembly can use standard components, which can reduce costs.

As shown in FIG. 3, in one or some embodiments, the cylinder assembly 24 includes a first cylinder 26 and a second cylinder 27. The first cylinder 26 is provided with a first piston 28 connected to the motor assembly 23, the first piston 28 moving under the driving of the motor assembly 23. The second cylinder 27 is provided with a second piston 29 connected to the ball-head structure 21. The first cylinder 26 and the second cylinder 27 are connected by means of a gas channel 30. Therefore, by means of the two cylinders (the first cylinder 26 and the second cylinder 27) connected in series, it can be ensured that a sufficiently large pressing force is provided for the pressing member to ensure a locking effect.

However, the present application is not limited thereto. For example, the cylinder assembly may alternatively include only one cylinder, three cylinders, or more cylinders, which may be set according to actual needs. In addition, although FIG. 3 shows that the two cylinders are disposed in series, the present application is not limited thereto. For example, two or more cylinders may be disposed in parallel as long as a sufficiently large pressing force can be provided for the pressing member.

In one or some embodiments, the cylinder assembly 24 may further include a first check valve 31 and a second check valve 32. The first check valve 31 is disposed in the gas passage 30 to allow a gas to flow unidirectionally from the first cylinder 26 into the second cylinder 27. The second check valve 32 is disposed on the first piston 28, and the second check valve 32 is configured to be closed when the first piston 28 compresses the gas in the first cylinder 26, and to be opened when the first piston 28 retracts.

Therefore, the first cylinder 26 may continuously press gas into the second cylinder as an inflator, and can sufficiently ensure that the second piston applies a sufficiently large pressing force to the pressing member, so that a locking effect can be ensured.

In this embodiment of the present application, the first check valve 31 and the second check valve 32 may use any existing check valve as long as a specific structure thereof can be referred to a related technique.

Figure 4:
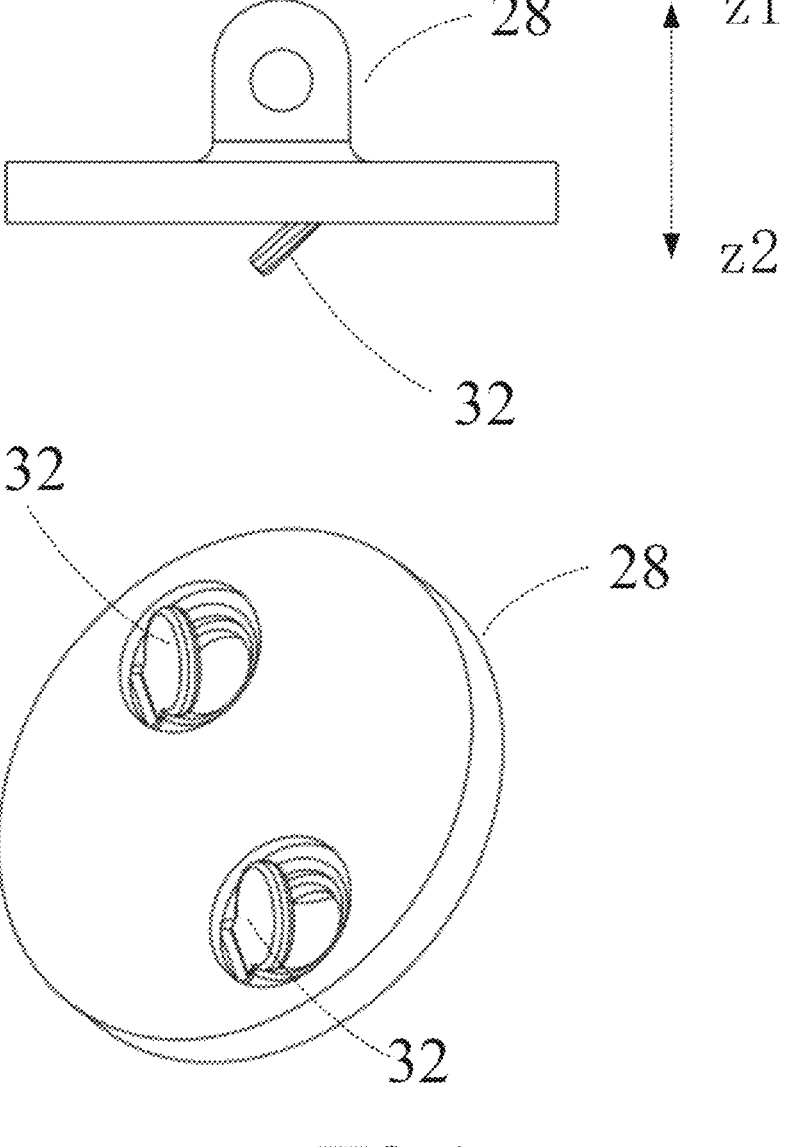
FIG. 4 shows a schematic diagram of a structure of a first piston according to an embodiment of the present application.

For example, FIG. 4 shows a schematic diagram of a structure of the first piston according to this embodiment of the present application. The upper part in FIG. 4 shows a case in which the first piston is viewed from the side, and the lower part in FIG. 4 shows a case in which the first piston is viewed in an oblique direction.

As shown in FIG. 4, the second check valve 32 is disposed on the first piston 28. When the first piston 28 is moved upward in a z1 direction of the vertical axis z under the action of the motor 33, a valve of the second check valve 32 is opened toward the inside of the piston under the action of a negative pressure, and gas enters the first piston 28. When the first piston 28 is moved downward in a z2 direction of the vertical axis z under the action of the motor 33, the second check valve 32 is closed, and the first piston 28 presses the gas in the piston into the second piston 29 by means of the gas passage 30, thereby driving the second piston 29.

In this embodiment of the present application, FIG. 4 shows that the first piston 28 is provided with two second check valves 32, but the present application is not limited thereto. The first piston 28 may include only one second check valve 32 or more than two second check valves 32, and a plurality of second check valves 32 may be disposed at symmetrical positions of the first piston 28.

In addition, for the first check valve 31, reference may be made to the foregoing description of the second check valve 32, and the description will not be repeated.

As shown in FIG. 3, in one or some embodiments, an inner diameter of the first cylinder 26 is smaller than an inner diameter of the second cylinder 27.

Therefore, when the first piston 28 applies pressure to the gas in the first cylinder 26, the gas in the first cylinder 26 enters the second cylinder 27 and acts on the second piston 29. Because the pressure of the gas is the same everywhere, when the inner diameter of the second cylinder 27 is greater than the inner diameter of the first cylinder 26, an acting force applied by the gas to the second piston 29 is greater than an acting force applied to the first piston 28. Specifically, an amplification ratio of an acting force is a ratio of a cross-sectional area of the second cylinder 27 to a cross-sectional area of the first cylinder 26. Therefore, an acting force can be magnified, thereby ensuring a locking effect.

In this embodiment of the present application, a specific value of a ratio of the inner diameter of the second cylinder 27 to the inner diameter of the first cylinder 26 or the ratio of the cross-sectional area of the second cylinder 27 to the cross-sectional area of the first cylinder 26 is not set. For example, the ratio of the cross-sectional area of the second cylinder 27 to the cross-sectional area of the first cylinder 26 may be 10, but the present application is not limited thereto, and the ratio may be another value and may be set to an appropriate value according to actual needs.

As shown in FIG. 3, in one or some embodiments, the motor assembly 23 includes a motor 33, a transmission gear 34, and a transmission rod 35, the transmission gear 34 being engaged with an output gear 36 of the motor 33, and both ends of the transmission rod 35 being connected to the transmission gear 34 and the cylinder assembly 24, respectively. Therefore, the output of the motor 33 can be converted into an acting force applied to the cylinder assembly 24 by means of a simple structure.

In this embodiment of the present application, when the scanning assembly needs to be locked, the motor 33 may continuously output. In this case, the first piston 28 moves reciprocally within the first cylinder 26 under the driving of the transmission rod 35, so that pressure can be continuously applied to the gas in the first cylinder. Therefore, an acting force can be continuously applied to the second piston 29 to ensure a pressing force applied by the pressing member to a spherical structure, and ensure reliability of locking the scanning assembly.

However, the present application is not limited thereto. For example, an output mode of the motor 33 may also be set, for example, the number of rotation cycles of the output gear 36 and/or a continuous rotation duration may be set, so that the acting force applied by the second piston 29 to the pressing member reaches a predetermined value to ensure a locking effect on the scanning assembly. This is not limited in the present application, and the output mode of the motor may be set according to actual needs.

In one or some embodiments, as shown in FIG. 3, a radial dimension of the transmission gear 34 is greater than a radial dimension of the output gear 36 of the motor 33. Therefore, a relatively fast rotating speed and a relatively small acting force of the motor 33 may be converted into a relatively large acting force applied to the transmission rod 35, so that a pressing force applied to the pressing member can be further improved, and the locking effect on the scanning assembly can be further improved.

In this embodiment of the present application, a specific ratio of the radial dimension of the output gear 36 of the motor 33 to the radial dimension of the transmission gear 34 is not specifically limited in the present application. For example, the specific ratio may be 5. However, the present application is not limited thereto, and a proper value may be set according to actual needs.

The following is an example analysis of an acting force applied to the second piston under the driving of the motor.

Figure 5:
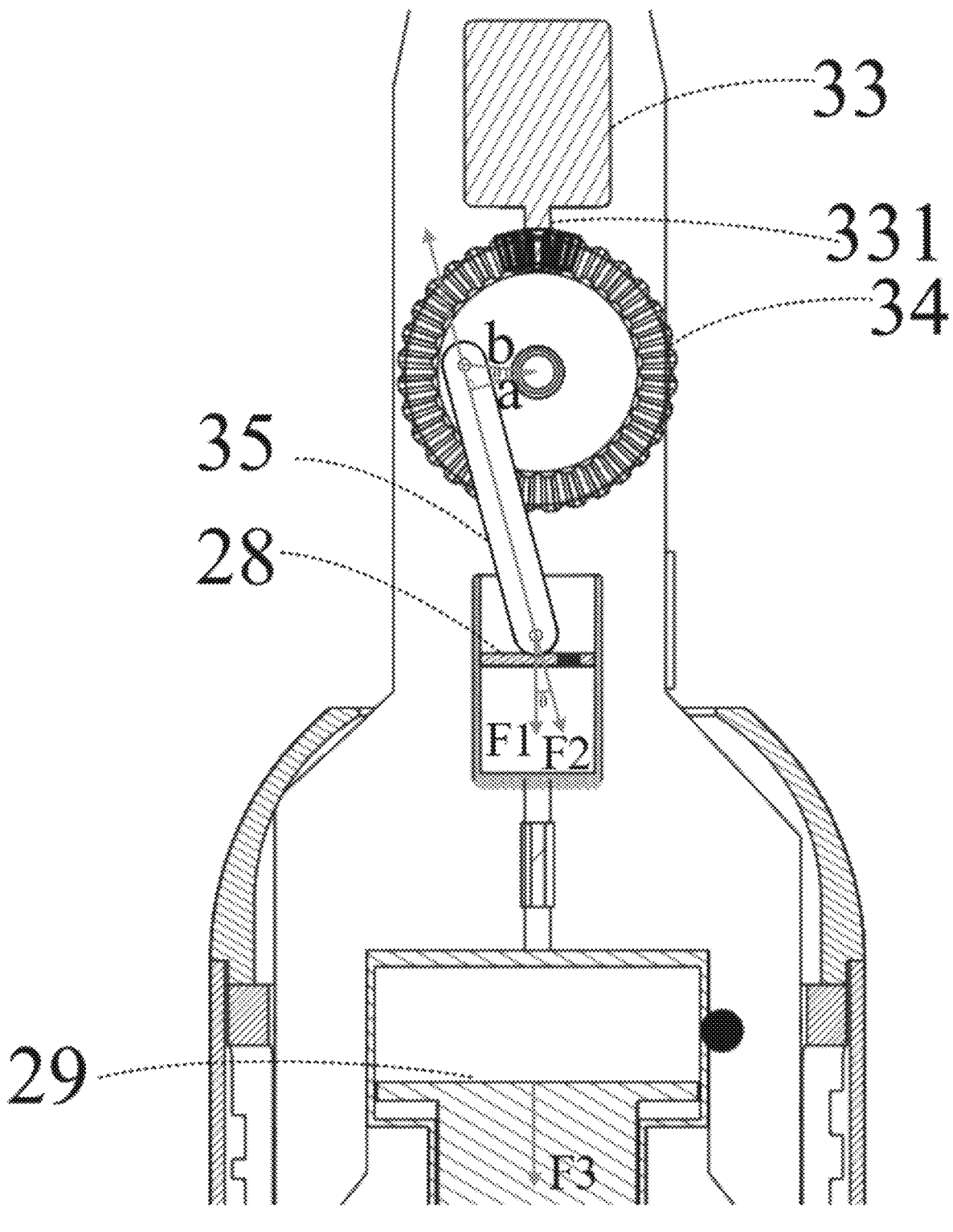
FIG. 5 shows a schematic diagram of a force analysis in a locking apparatus.

FIG. 5 shows a schematic diagram of a force analysis in a locking apparatus.

As shown in FIG. 5, F2 is an acting force applied by one end that is of the transmission rod 35 and that is in contact with the first piston 28, F1 is a vertical downward acting force applied by the transmission rod 35 to the first piston 28, wherein when there is an included angle $\theta$ between a length direction of the transmission rod 35 and a vertical downward direction ($0°<\theta<90°$), F1 is equal to F2 multiplied by cos $\theta$, that is, $F1=F2*\cos\theta$.

In addition, if an output torque of the output gear 36 of the motor 33 is T and an output torque of the transmission gear 34 is 5T, a vertical line is made from the center of the transmission gear 34 toward the transmission rod 35, and the length of the vertical line is set to a. In this case, F2 is equal to 5T divided by a, that is, $F2=5T/a$. A straight line is made from the center of the transmission gear 34 in a direction having an included angle $\theta$ with the vertical line and intersects the transmission gear 34. Assuming that a length from an intersection point to the center of the transmission gear 34 is b, that is, $b*\cos\theta=a$, $F1=F2*\cos\theta=(5T/a)*\cos\theta=5T/(b*\cos\theta)*\cos\theta=5T/b$.

Therefore, the minimum value of a vertically downward acting force F1 applied by the transmission rod 35 to the first piston 28 is $F1_{min}=5T/b_{max}=5T/(a_{max}/\cos\theta)$. Because a is a vertical line distance from the center of the transmission gear 34 to the transmission rod 35, it can be learned that the maximum value of a is the radius R of the transmission gear 34. Therefore, $F1_{min}=5T/(R/\cos\theta)$.

In some examples, that the output torque of the output gear of the motor 33 is T=0.24 N·m, the radius of the transmission gear 34 is R=4 mm=0.004 m, and $\theta=45°$ is used as an example for calculation, to obtain $F1_{min}=150$ N. In addition, that the ratio of a cross-sectional area of the second piston 29 to a cross-sectional area of the first piston 28 is 10 is used as an example, and F3=150 N×10=1500 N. Therefore, even if an acting force output by the motor 33 is relatively small, the acting force can be amplified into a sufficient large acting force by means of the locking apparatus in this embodiment of the present application, so that the second piston 29 can reliably press the pressing member, thereby implementing reliable locking.

It should be noted that the specific values in the foregoing description with respect to FIG. 5 and proportions between components are merely example descriptions, to facilitate a better understanding of some of the reasons why the locking apparatus in the present application can quickly provide a stable locking force. However, the present application is not limited thereto.

In this embodiment of the present application, a position at which the transmission rod 35 is disposed on the transmission gear 34 is not limited. For example, an end portion that is of the transmission rod 35 and that is connected to the transmission gear 34 may be disposed at a position near an edge of the transmission gear 34. Therefore, compared with a case in which the end portion of the transmission rod 35 is disposed near the center of the transmission gear 34, the transmission rod 35 can apply a larger stroke to the first piston 28 as the end portion of the transmission rod 35 is farther from the center of the transmission gear 34 when the transmission rod 35 is rotated around the transmission gear 34 by a predetermined angle, thereby further increasing the pressing force applied to the pressing member and further increasing the locking effect on the scanning assembly.

In addition, a distance between the end portion that is of the transmission rod 35 and that is disposed on the transmission gear 34 and the center of the transmission gear 34 may be set to a predetermined value, to ensure the pressing force applied to the pressing member. For example, the distance may be set to 4 millimeters, but the present application is not limited thereto, and the distance may be set to another value and may be set according to actual needs.

In the present application, the motor assembly 23 may be an unnecessary structure. In this case, an acting force may be manually applied to the cylinder assembly 24. Therefore, costs of a product can be reduced.

In this embodiment of the present application, the length of the transmission rod 35 is not specifically limited, and may be set according to actual needs.

According to the foregoing embodiment, a relatively small output force of the output gear 36 of the motor can be amplified once or a plurality of times to become an acting force for ensuring the pressing effect on the pressing member, thereby ensuring the locking effect on the scanning assembly.

In one or some embodiments, the locking apparatus further includes a pressure limiting valve disposed on the cylinder, the pressure limiting valve being opened when gas pressure in the cylinder reaches a predetermined value. Therefore, even if the motor assembly continuously outputs an acting force to the cylinder assembly, damage to a device due to an excessive acting force applied to the pressing member can also be prevented.

In embodiments of the present application, the pressure limiting valve may be disposed at a portion that is of the second cylinder and that is close to the pressing member. For example, the pressure limiting valve may be disposed at the bottom of the second cylinder, or disposed at a wall portion that is of the second cylinder and that is close to the pressing member.

In one or some embodiments, the pressure limiting valve is a solenoid valve that can be switched between an open state and a closed state by means of a switch. Therefore, damage to a device due to an excessive acting force applied to the pressing member can be prevented, and operations of locking or unlocking the scanning assembly can be implemented simply by means of an operation of pressing the switch, thereby further reducing burdens on an operator.

However, the present application is not limited thereto. The pressure limiting valve may alternatively be another type of valve member, which is not limited in the present application.

In embodiments of the present application, a specific structure of the pressing member is not limited. For example, a portion that is of the pressing member and that presses against the cylinder assembly may be a flat surface to ensure an abutting effect, and the inside of the pressing member may be, for example, a hollow spherical shape surrounding at least a part of the ball-head structure. Therefore, a sufficient contact area with the ball-head structure can be ensured to provide a reliable friction force.

It can be learned from the foregoing embodiment that, driven by the motor assembly 23, the cylinder assembly 24 drives the pressing member 25 to press against the ball-head structure 21 to lock the scanning assembly, so that the structure is simple and highly reliable, and costs can be reduced.

So far, various implementations of the locking apparatus for the scanning assembly in the ultrasound imaging apparatus have been described in detail in the above embodiments of the present application. In another embodiment, the present application further shows an ultrasound imaging apparatus. The ultrasound imaging apparatus includes the locking apparatus described in any of the above embodiments.

In addition to the locking apparatus, other components of the ultrasound imaging apparatus may refer to other embodiments described above, for example, any of the embodiments shown by FIG. 1, FIG. 2, and the like. In some embodiments, the ultrasound imaging apparatus further includes: a scanning assembly, the scanning assembly being connected to the locking apparatus and including a housing, an ultrasound transducer, and a control unit. The control unit is disposed outside the housing and is operable to control the locking apparatus. The ultrasound transducer is accommodated within the housing and is configured to perform ultrasound imaging.

It should be noted that the foregoing FIG. 1 to FIG. 5 only schematically illustrate the ultrasound imaging apparatus and the locking apparatus in the embodiments of the present application. However, the present application is not limited thereto. For specific content of each structure or component, refer to related techniques. In addition, structures or components that are not shown in FIG. 1 to FIG. 5 may be added, or one or more structures or components in FIG. 1 to FIG. 5 may be reduced. For components or elements not particularly specified in FIG. 1 to FIG. 5, reference may be made to the related techniques, which is not limited by the present application.

The above embodiments merely provide illustrative descriptions of the embodiments of the present application. However, the present application is not limited thereto, and appropriate variations may be made on the basis of the above embodiments. For example, each of the embodiments described above may be used independently, or one or more among the above embodiments may be combined.

The present application is described above with reference to specific embodiments. However, it should be clear to those skilled in the art that the foregoing description is merely illustrative and is not intended to limit the scope of protection of the present application. Various variations and modifications may be made by those skilled in the art according to the spirit and principle of the present application, and these variations and modifications also fall within the scope of the present application.

Preferred embodiments of the present application are described above with reference to the accompanying drawings. Many features and advantages of the embodiments are clear according to the detailed description. Therefore, the appended claims are intended to cover all these features and advantages that fall within the true spirit and scope of these embodiments. In addition, as many modifications and changes could be easily conceived of by those skilled in the art, the embodiments of the present application are not limited to the illustrated and described precise structures and operations, but can encompass all appropriate modifications, changes, and equivalents that fall within the scope of the embodiments.

The invention claimed is:

1. A locking apparatus for a scanning assembly in an ultrasound imaging apparatus, comprising:
   a scanning assembly connecting apparatus having a ball-head structure on a first end and a second end connected to the scanning assembly;
   a fixing member, connected to a main body of the ultrasound imaging apparatus, and comprising a hollow cavity, the ball-head structure being accommodated within the hollow cavity and movable within the hollow cavity;
   a pressing assembly, comprising a motor assembly, a cylinder assembly, and a pressing member, the cylinder assembly being disposed between the motor assembly and the pressing member, and cylinder gas pressure of the cylinder assembly being increased under the driving of the motor assembly, to drive the pressing member to press against the ball-head structure, thereby locking the scanning assembly; and
   a pressing assembly housing surrounding the pressing assembly,
   wherein the pressing assembly housing and the fixing member provide a common housing containing the pressing assembly and at least a portion of the ball-head structure.

2. The locking apparatus according to claim 1, wherein the cylinder assembly comprises:
   a first cylinder, provided with a first piston connected to the motor assembly, the first piston moving under the driving of the motor assembly; and
   a second cylinder, provided with a second piston connected to the ball-head structure;
   the first cylinder being connected to the second cylinder by means of a gas passage.

3. The locking apparatus according to claim 2, wherein the cylinder assembly further comprises:
   a first check valve, disposed in the gas passage to allow gas to flow unidirectionally from the first cylinder into the second cylinder; and
   a second check valve, disposed on the first piston, the second check valve being configured to be closed when the first piston compresses the gas in the first cylinder, and to be opened when the first piston retracts.

4. The locking apparatus according to claim 2, wherein an inner diameter of the first cylinder is smaller than an inner diameter of the second cylinder.

5. The locking apparatus according to claim 1, wherein the motor assembly comprises a motor, a transmission gear, and a transmission rod, the transmission gear being engaged with an output gear of the motor, and both ends of the transmission rod being connected to the transmission gear and the cylinder assembly, respectively.

6. The locking apparatus according to claim 5, wherein a radial dimension of the transmission gear is greater than a radial dimension of the output gear of the motor.

7. An ultrasound imaging apparatus, comprising:
an ultrasound transducer; and
a locking apparatus, comprising:
   a scanning assembly connecting apparatus having a ball-head structure on a first end and a second end connected to the scanning assembly;
   a fixing member, connected to a main body of the ultrasound imaging apparatus, and comprising a hollow cavity, the ball-head structure being accommodated within the hollow cavity and movable within the hollow cavity;
   a pressing assembly, comprising a motor assembly, a cylinder assembly, and a pressing member, the cylinder assembly being disposed between the motor assembly and the pressing member, and cylinder gas pressure of the cylinder assembly being increased under the driving of the motor assembly, to drive the pressing member to press against the ball-head structure, thereby locking the scanning assembly; and
   a pressing assembly housing surrounding the pressing assembly,
   wherein the pressing assembly housing and the fixing member provide a common housing containing the pressing assembly and at least a portion of the ball-head structure.

8. The ultrasound imaging apparatus according to claim 7, further comprising:
   a scanning assembly, the scanning assembly being connected to the locking apparatus and comprising a housing, an ultrasound transducer, and a control unit, the control unit being disposed outside the housing and being operable to control the locking apparatus, and the ultrasound transducer being accommodated within the housing and configured to perform ultrasound imaging.

9. The locking apparatus according to claim 7, wherein the cylinder assembly comprises:
   a first cylinder, provided with a first piston connected to the motor assembly, the first piston moving under the driving of the motor assembly; and
   a second cylinder, provided with a second piston connected to the ball-head structure;
   the first cylinder being connected to the second cylinder by means of a gas passage.

10. The locking apparatus according to claim 9, wherein the cylinder assembly further comprises:
   a first check valve, disposed in the gas passage to allow gas to flow unidirectionally from the first cylinder into the second cylinder; and
   a second check valve, disposed on the first piston, the second check valve being configured to be closed when the first piston compresses the gas in the first cylinder, and to be opened when the first piston retracts.

11. The locking apparatus according to claim 9, wherein an inner diameter of the first cylinder is smaller than an inner diameter of the second cylinder.

12. The locking apparatus according to claim 7, wherein the motor assembly comprises a motor, a transmission gear, and a transmission rod, the transmission gear being engaged with an output gear of the motor, and both ends of the transmission rod being connected to the transmission gear and the cylinder assembly, respectively.

13. The locking apparatus according to claim 12, wherein a radial dimension of the transmission gear is greater than a radial dimension of the output gear of the motor.

14. The locking apparatus according to claim 7, further comprising a pressure limiting valve disposed on the cylinder, the pressure limiting valve being opened when gas pressure in the cylinder reaches a predetermined value.

15. The locking apparatus according to claim 14, wherein the pressure limiting valve is a solenoid valve that can be switched between an open state and a closed state by means of a switch.

* * * * *